United States Patent
Arkles et al.

(10) Patent No.: US 10,479,806 B2
(45) Date of Patent: Nov. 19, 2019

(54) HYDRIDOSILAPYRROLES, HYDRIDOSILAAZAPYRROLES, THIASILACYCLOPENTANES, METHOD FOR PREPARATION THEREOF, AND REACTION PRODUCTS THEREFROM

(71) Applicant: Gelest Technologies, Inc., Morrisville, PA (US)

(72) Inventors: Barry C. Arkles, Pipersville, PA (US); Youlin Pan, Langhorne, PA (US); Fernando Jove, Collingswood, NJ (US)

(73) Assignee: Gelest Technologies, Inc., Morrisville, PA (US)

( * ) Notice: Subject to any disclaimer, the term of this patent is extended or adjusted under 35 U.S.C. 154(b) by 0 days.

(21) Appl. No.: 15/728,606

(22) Filed: Oct. 10, 2017

(65) Prior Publication Data

US 2018/0030071 A1 Feb. 1, 2018

Related U.S. Application Data

(62) Division of application No. 15/176,703, filed on Jun. 8, 2016, now Pat. No. 9,815,858.

(60) Provisional application No. 62/180,351, filed on Jun. 16, 2015.

(51) Int. Cl.
| | | |
|---|---|---|
| *C07F 7/10* | (2006.01) | |
| *C07F 7/08* | (2006.01) | |
| *H01L 21/02* | (2006.01) | |
| *C01B 21/068* | (2006.01) | |
| *C01B 21/082* | (2006.01) | |

(52) U.S. Cl.
CPC .............. *C07F 7/10* (2013.01); *C01B 21/068* (2013.01); *C01B 21/0828* (2013.01); *C07F 7/0898* (2013.01); *H01L 21/0217* (2013.01); *H01L 21/02167* (2013.01); *H01L 21/02219* (2013.01)

(58) Field of Classification Search
None
See application file for complete search history.

(56) References Cited

U.S. PATENT DOCUMENTS

| | | | |
|---|---|---|---|
| 4,200,666 | A | 4/1980 | Reinberg |
| 6,586,056 | B2 | 7/2003 | Arkles et al. |
| 2010/0016496 | A1 | 1/2010 | Tanaka et al. |
| 2011/0256734 | A1 | 10/2011 | Hausmann et al. |

FOREIGN PATENT DOCUMENTS

| | | |
|---|---|---|
| EP | 0499409 A1 | 8/1992 |
| EP | 2644609 A2 | 10/2013 |
| JP | 2002069082 A | 3/2002 |
| JP | 2015096489 A | 5/2015 |
| WO | 2008033980 A2 | 3/2008 |

OTHER PUBLICATIONS

Arkles—J. Electrochem. Soc., 1986, 233-234. (Year: 1986).*
Arkles, J. Electrochemical Soc., vol. 133, No. 1, pp. 233-234 (1986). (Year: 1986).*
Hochberg et al, "Diethylsilane as a Silcon Source for The Deposition of Silicon Nitride and Silicon Oxynitride Films by LPCVD", Mat. Res. Soc. Symp. Proc.; 204(509), pp. 509-514 (1991).
Arkles, "Silicon Nitride from Organosilazane Cyclic and Linear Prepolymers", Journal of the Electrochemical Society; 133(1) pp. 233-234 (1986).
Tanaka et al, "Film Properties of Low-k Silicon Nitride Films Formed by Hexachlorodisilane and Ammonia", Journal of the Electrochemical Society; 147(6) pp. 2284-2289 (2000).
Gumpher et al, "Characterization of Low-Temperature Silicon Nitride LPCVD from Bis(tertiary-butylamino)silane and Ammonia", Journal of the Electrochemical Society; 151(5) pp. 353-359 (2004).
Arkles et al, "Cyclic azasilanes: volatile coupling agents for nano-technology", Silanes and Other Coupling Agents; vol. 3 pp. 179-191 Ed. K.L. Mittal (2004).
Int'l Search Report and Written Opinion dated Jul. 26, 2016 in Int'l Application No. PCT/US2016/036719.
Wille et al., "A Computational Study of Multicomponent Orbital Interactions During the Cyclization of Silyl, Germyl, and Stannyl Radicals onto C—N and C—O Multiple Bonds", Journal of Organic Chemistry, vol. 73, No. 15, 2 pgs. (Aug. 2008).
Gornowicz et al., "Preparation of Silylalkanethiols", Journal of Organic Chem., vol. 33, No. 7, 1 pg. (Jan. 1968).
Tanaka et al., "Production of Modified Conjugated Diene Polymers, Modified Conjugated Diene Polymers Produced by the Process, Rubber Compositions, and Tires", Chemical Abstract Service, 2pgs (2015).
Zuckerman et al., "The Formation of the Bonds Between Hydrogen and C, Si, Ge, Sn, Pb", Inorganic Reactions and Methods, p. 106 (2009).
Office Action dated Apr. 13, 2017 in U.S. Appl. No. 15/176,703, by Arkles.
Office Action dated May 19, 2017 in U.S. Appl. No. 15/176,703, by Arkles.
CA Registry Entry, RN 16456-13-6 (Nov. 16, 1984).

(Continued)

*Primary Examiner* — Clinton A Brooks
*Assistant Examiner* — Kofi Adzamli
(74) *Attorney, Agent, or Firm* — Panitch Schwarze Belisario & Nadel LLP

(57) ABSTRACT

Hydridosilapyrroles and hydridosilaazapyrrole are a new class of heterocyclic compounds having a silicon bound to carbon and nitrogen atoms within the ring system and one or two hydrogen atoms on the silicon atom. The compounds have formula (I):

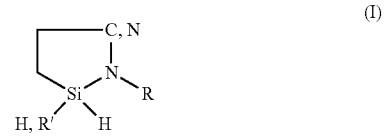

in which R is a substituted or unsubstituted organic group and R' is an alkyl group. These compounds react with a variety of organic and inorganic hydroxyl groups by a ring-opening reaction and may be used to produce silicon nitride or silicon carbonitride films.

1 Claim, No Drawings

(56) References Cited

OTHER PUBLICATIONS

Shainyan et al., "1,3-Dimethyl-3-silapiperidine: Synthesis, Molecular Structure, and Conformational Analysis by Gas-Phase Electron Diffraction, Low Temperature NMR, IR and Raman Spectroscopy, and Quantum Chemical Calculations", J. Org. Chem., vol. 78, No. 8, pp. 3939-3947 (2013).
Int'l Preliminary Report on Patentability dated Dec. 19, 2017 in Int'l Application No. PCT/US2016/036719.
Office Action dated Apr. 13, 2017 in U.S. Appl. No. 15/176,703, Arkles.
Office Action dated May 19, 2017 in U.S. Appl. No. 15/176,703, Arkles.
Office Action dated Sep. 27, 2018 in EP Application No. 16732419.3.
Kassaee et al., "Stable silylenes with acyclic, cyclic, and unsaturated cyclic structures: Effects of heteroatoms and cyclopropyl a-substituents at DFT," Journal of Organometallic Chemistry, vol. 696, pp. 2059-2064 (2011).
Notice of Allowance dated May 30, 2018 in U.S. Appl. No. 15/728,634, by Arkles.
Office Action dated Dec. 11, 2018 in JP Application No. 2017564620.
Office Action dated Mar. 20, 2019 in EP Application No. 16732419.3.
Office Action dated Apr. 12, 2019 in KR Application No. 10-2018-7001385.
Office Action dated Sep. 3, 2019 in JP Application No. 2017564620.

\* cited by examiner

HYDRIDOSILAPYRROLES, HYDRIDOSILAAZAPYRROLES, THIASILACYCLOPENTANES, METHOD FOR PREPARATION THEREOF, AND REACTION PRODUCTS THEREFROM

CROSS-REFERENCE TO RELATED APPLICATION

This application is a divisional of co-pending U.S. patent application Ser. No. 15/176,703, filed Jun. 8, 2016, which claims priority to U.S. Provisional Application No. 62/180,351, filed Jun. 16, 2015, the disclosures of which are herein incorporated by reference in their entireties.

BACKGROUND OF THE INVENTION

There is currently a great deal of interest in molecular layer deposition for nano-featured devices, including semiconductors and microelectromechanical systems (MEMS). Rapid and preferably quantitative deposition of single molecular layers with a minimum of byproducts is desirable. Silicon carbonitride films are of particular interest for a variety of dielectric, passivation and etch-stop applications.

Examples of known systems to produce silicon nitride or silicon carbonitride films include that described in U.S. Pat. No. 4,200,666 using trisilylamine ($(SiH_3)_3N$) and an inert gas with optional ammonia; the system of diethylsilane and ammonia in an LPCVD system at 800° C. as described in A. Hochberg et al. (*Mat. Res. Soc. Symp,* 24, 509 (1991)); and the system of cyclic silazanes and ammonia in a chemical vapor deposition (CVD) process described by B. Arkles (*J. Electrochemical Soc.*, Vol. 133, No. 1, pp. 233-234 (1986)).

More recently, halide-containing precursors such as tetraiodosilane and hexachlorodisilane have been described in U.S. Pat. No. 6,586,056 and by M. Tanaka et al. (*J. Electrochemical Society,* 147, 2284 (2000)), respectively. Unfortunately, there are operational difficulties associated with the corrosiveness of the precursors, as well as with film contaminants and byproducts.

Another approach is the use of bis(t-butylamino)silane, which produces SiN films of reasonable quality at temperatures as low as 550° C. (J. Gumpher et al., *J. Electrochem. Soc.,* 151, G353 (2004)) or in a plasma-assisted pulsed deposition method as described in U.S. Patent Application Publication No. 2011/0256734. In both cases, there are complications with carbon contamination of films and the high energy requirements of both the thermal and plasma regimes, which are not compatible with substrate stability. A review of other alternative approaches is found in EP 2 644 609 A2, which suggests fluorinated precursors. While such fluorinated precursors theoretically allow lower deposition temperatures, the introduced fluorine frequently affects electrical properties of silicon based structures.

Known cyclic azasilanes contain alkyl (e.g., methyl) or alkoxy (e.g., ethoxy) substitution on the silicon atom (see B. Arkles et al., "Cyclic Azasilanes: Volatile Coupling Agents for Nanotechnology" in *Silanes and Other Coupling Agents,* Vol. 3, K. Mittal (Ed.) VSP (Brill), pp. 179-191 (2004)). In the primary applications of interest, these compounds are unacceptable because they either contain excessive levels of carbon or introduce oxygen into the film due to substitution at the silicon atom on the ring. Thus, the need for new silicon nitride and silicon carbonitride precursors that deposit silicon nitrides at low temperature has still not been satisfied.

BRIEF SUMMARY OF THE INVENTION

A hydridosilapyrrole or hydridosilaazapyrrole according to an embodiment of the invention has formula (I):

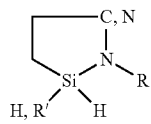

wherein R is a substituted or unsubstituted organic group having a carbon or silicon atom bonded to the pyrrole ring nitrogen and R' is an alkyl group.

A method of producing a hydridosilapyrrole or hydridosilaazapyrrole having formula (I):

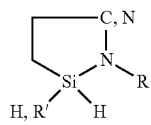

wherein R is a substituted or unsubstituted organic group having a carbon or silicon atom bonded to the pyrrole ring nitrogen and R' is an alkyl group, the method comprising reducing a cyclic azasilane having an alkoxide group on the silicon.

A thiasilacyclopentane having formula (II):

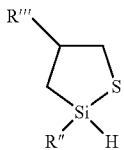

wherein R" and R''' are independently hydrogen or an alkyl group.

DETAILED DESCRIPTION OF THE INVENTION

The invention is directed to a new class of cyclic azasilanes known as hydridosilapyrroles (or cyclic azasilylhydrides) and hydridoazapyrroles. Unlike known cyclic azasilanes which contain alkyl or alkoxy substituents on the silicon atom, the inventive materials are a class of hydridosilanes which can reduce or eliminate the carbon and oxygen contributions from substitution on the silicon atom.

The hydridosilapyrroles and hydridoazapyrroles according to the invention have a general structure shown in formula (I):

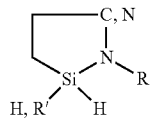

Essential features of these compounds include a five atom ring structure in which a silicon atom within the ring is bonded to both a carbon and a nitrogen atom and at least one hydrogen atom is bonded to the silicon atom. As shown in Formula (I), the nitrogen may be bonded to a carbon or to a second nitrogen in the ring, forming a cyclic diazasilane (also called a hydridosilaazapyrrole or diazasilacyclopentane).

In formula (I), R may be any substituted or unsubstituted organic group in which a carbon or silicon is bonded to the ring nitrogen. Exemplary groups include, without limitation, alkyl groups, aryl groups, esters, chiral organic groups and trimethylsilyl groups. Preferred are small hydrocarbon radicals having up to six carbon atoms (including phenyl) and nitrogen-substituted hydrocarbons such as dimethylaminoethyl. R' may be any alkyl group preferably having up to about twenty carbon atoms, more preferably less than about six carbon atoms, most preferably methyl, ethyl, propyl, or butyl.

Simple specific examples of inventive compounds include N-methyl-2-silapyrrole and N-butyl-2-silapyrrole:

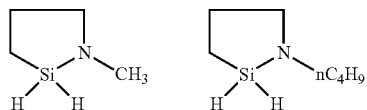

Other examples include those having more complex functional substitutions at the nitrogen, including chiral phenethylamines, trimethylsilyl groups and tertiary amine groups.

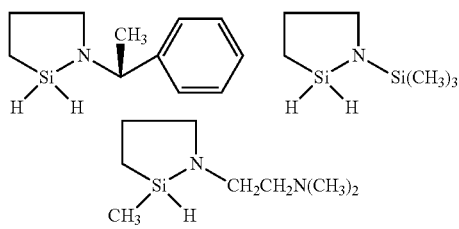

In one embodiment, the ring structure also contains an additional nitrogen atom in the 3 position, forming cyclic diazasilanes. Two exemplary cyclic diazasilanes include:

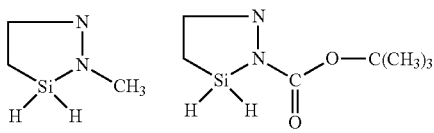

The invention also relates to a method for producing the hydridosilapyrroles described above. The method involves reducing the corresponding cyclic azasilanes having alkoxide substitution on the silicon atom, as shown in the following exemplary scheme:

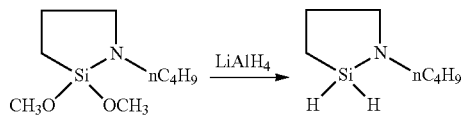

Thus, the only limitation on the hydridosilapyrroles which may be produced according to the method of the invention is the ability to synthesize the alkoxy-containing precursor.

The inventive materials react quantitatively via a ring-opening reaction with both inorganic and organic hydroxyl groups, including hydroxyl groups on siliceous, aluminum, and titanium substrates, as shown below, and with organic hydroxyl groups, including alcohols.

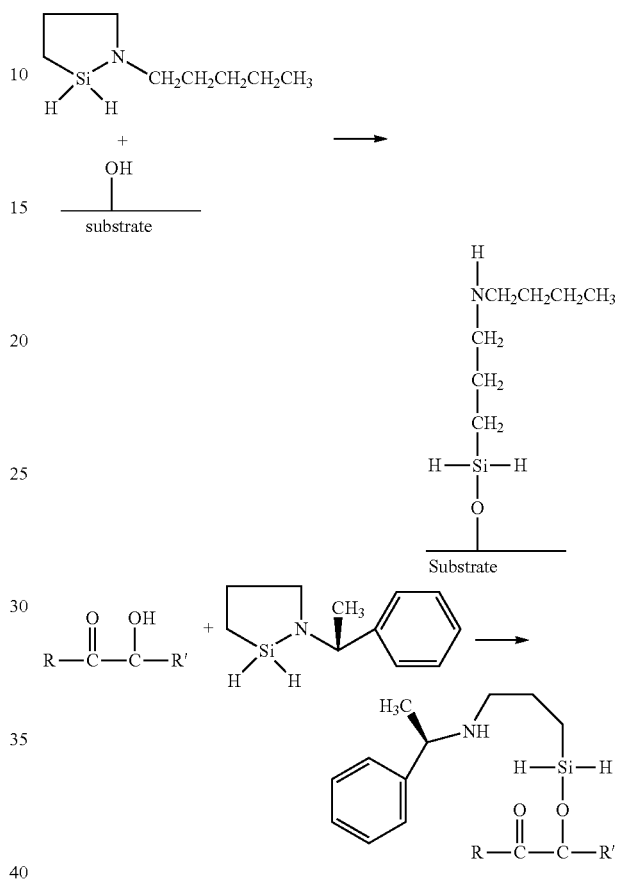

These materials may also react with isolated silanols, such as triethylsilanol, in homogeneous solutions, and are also capable of reacting with other protic species, including amines and mercaptans.

The silyl hydride functionality may remain intact or, depending on the desired end-product, may be dehydrogenated to form silicon carbonitrides, may be utilized as a regiospecific reducing agent, or may undergo hydrosilylation. Thus, the inventive materials are attractive for many applications, including the formation of silicon nitride and silicon carbonitride films.

The invention also relates to a new class of thiasilacyclopentane compounds having formula (II):

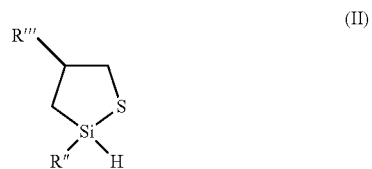

In Formula (II), R" and R'" are independently hydrogen or an alkyl group containing about one to about twenty carbon atoms, most preferably hydrogen or methyl. A preferred compound of this class is 1-thia-2-silacyclopentane shown below; other preferred and exemplary compounds of this class are also shown below. In these structures, R" and R'" are preferably hydrogen or methyl:

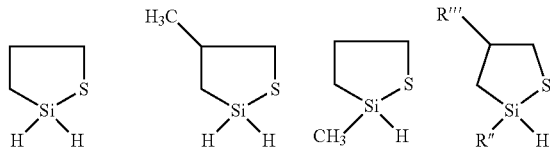

Thiasilacyclopentanes undergo reactions with hydroxylic surfaces generating films containing mercaptan groups. The mercapto groups formed in this reaction can reacted with olefins or other mercapto-compounds to further modify the surfaces.

The thiasilacyclopentane compounds according to the invention are described by a method which is analogous to that described above for producing hydridosilapyrroles: by the reduction of thiasilacyclopentane compounds having alkoxide group(s) on the silicon. For example, 1-thia-2-silacyclopentane is prepared from 2,2-alkoxy-1-thia-2-silacyclopentane, shown below, as a starting material:

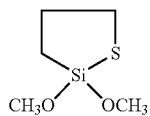

The invention will now be described in connection with the following non-limiting examples.

Example 1: Synthesis of N-butyl-2-silapyrrole (n-Butyl-azasilacyclopentane)

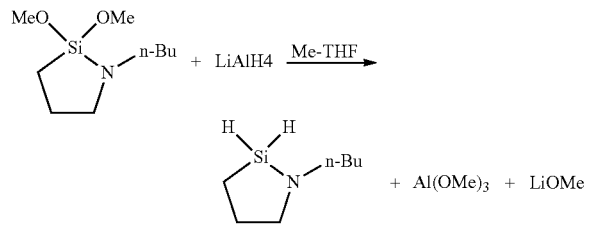

Under an argon atmosphere, a 2-liter 4-necked flask equipped with a cooling bath, mechanical stirrer, pot thermometer, addition funnel, and dry-ice distill head was charged with 400 ml of 2-methyltetrahydrofuran, followed by 25.3 g (0.67 mol) of lithium aluminum hydride portion wise. The mixture was cooled to −10° C. and 203.4 g (1.0 mol) N-n-butyl-aza-dimethoxysilacyclopentane were added via addition funnel between −5 to 0° C. over 2 hours. After completion of the addition, the pot mixture was maintained at 0° C. for about 2 hours. 345 g of mineral oil was added into the pot. The pot mixture was stripped at a pot temperature of 80° C. at 0.5 mmHg. Redistillation of the crude product under reduced pressure provided 68.1 g (48% yield) of the title compound, b.p.: 60²/25 mmHg, density@20° C.:0.783, FTIR: vS-H:2120.0 (vs).

Example 2: Synthesis of N-(3-Dimethylaminopropyl)-2-methyl-2-silapyrrole (N-Dimethylaminopropyl-Aza-1-Methyl-silacyclopentane)

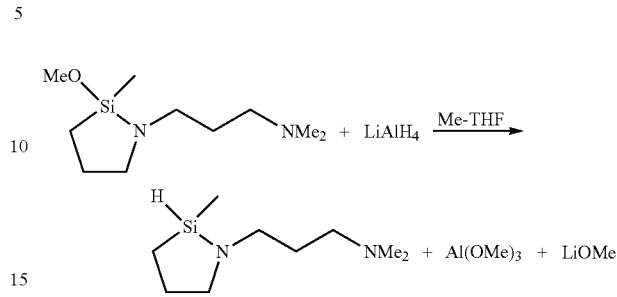

Under an argon atmosphere, a 2-liter 4-necked flask equipped with a cooling bath, mechanical stirrer, pot thermometer, addition funnel, and dry-ice distill head was charged with 300 ml of 2-methyltetrahydrofuran, followed by 9.5 g (0.25 mol) of lithium aluminum hydride portion wise. The mixture was cooled to −10° C. and 162.3 g (0.75 mol) N-n-dimethylaminopropyl-aza-methylmethoxysilacyclopentane was added via addition funnel between −5 and 0° C. over 2 hours. Upon completion of the addition, the pot mixture was kept at 0° C. for about 2 hours. 260 g of mineral oil was added into the pot. The pot mixture was stripped at a pot temperature of 80° at 0.5 mmHg. Redistillation of product crude under reduced pressure provided the title compound, b.p.: 52-4/0.5 mmHg, density@20° C.: 0.857, FTIR: vS-H:2111 (vs).

Example 3: Synthesis of N-Trimethylsilyl-2-silapyrrole (N-Trimethylsilyl-Aza-1-Methyl-Silacyclopentane)

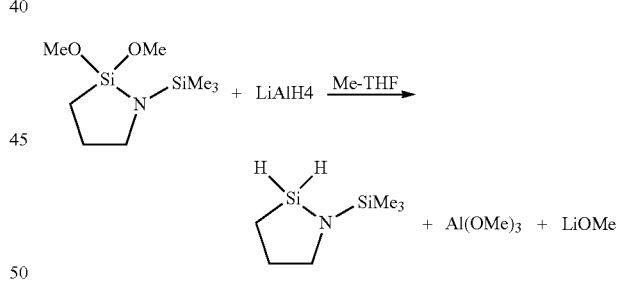

Under an argon atmosphere, a 2-liter 4-necked flask equipped with a cooling bath, mechanical stirrer, pot thermometer, addition funnel, and dry-ice distill head was charged with 400 ml of 2-methyltetrahydrofuran, followed by 25.3 g (0.67 mol) of lithium aluminum hydride portion wise. The mixture was cooled to −10° C. and 203.4 g (1.0 mol) N-trimethylsilyl-aza-dimethoxysilacyclopentane was added via addition funnel between −5 to 0° C. over 2 hours. Upon completion of the addition, the pot mixture was kept at 0° C. for about 2 hours. 345 g of mineral oil was added into the pot. The pot mixture was stripped at a pot temperature of 80° at 0.5 mmHg. Redistillation of product crude under reduced pressure provided the title compound, b.p.: 48-50/10 mmHg, density@20° C.: 0.846, FTIR: vS-H:2120 (vs).

Example 4: Synthesis of 1-Thia-2-silacyclopentane

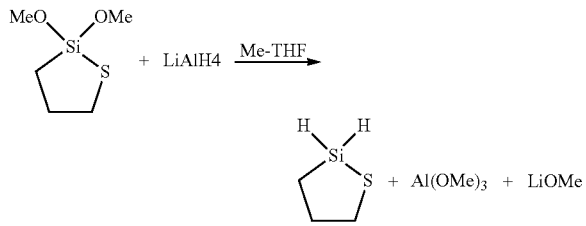

Under an argon atmosphere, a 2-liter 4-necked flask equipped with a cooling bath, mechanical stirrer, pot thermometer, addition funnel, and dry-ice distill head was charged with 490 ml of diglyme, followed by 27.8 g (0.0.73 mol) of lithium aluminum hydride portion wise. The mixture was cooled to −10° C. and 200.4 g (1.22 mol) of 2,2-dimethoxy-1-thia-2-silacyclopentane was added via addition funnel between −5 to 0° C. over 2 hours. Upon completion of the addition, the pot mixture was kept at 0° C. for about 2 hours. The pot mixture was stripped at a pot temperature of below 80° C. at 0.5 mmHg. Redistillation of product crude under reduced pressure provided the title compound which contained ~50% of diglyme: b.p.: 55/1.2 mmHg, density@20° C.: 0.827, FTIR: vS-H:2140 (vs).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silicon nitride or silicon carbonitride film produced from a hydridosilapyrrole or hydridosilaazapyrrole having formula (I):

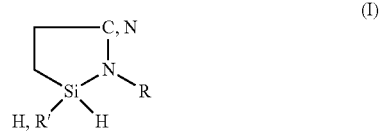

wherein R is a substituted or unsubstituted organic group having a carbon or silicon bonded to the ring nitrogen and R' is an alkyl group.

* * * * *